(12) United States Patent
Fiser et al.

(10) Patent No.: US 8,506,528 B2
(45) Date of Patent: *Aug. 13, 2013

(54) LOCKING CLIP WITH TRIGGER BUSHING

(75) Inventors: Richard Fiser, Kirkwood, MO (US); James L. Carlyon, Farmington, MO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/195,342

(22) Filed: Aug. 1, 2011

(65) Prior Publication Data

US 2011/0282280 A1    Nov. 17, 2011

Related U.S. Application Data

(63) Continuation of application No. 11/895,597, filed on Aug. 24, 2007, now Pat. No. 7,988,664, which is a continuation-in-part of application No. 10/585,987, filed as application No. PCT/US2004/036339 on Nov. 1, 2004, now Pat. No. 7,736,332, which is a continuation of application No. 10/698,869, filed on Oct. 31, 2003, now Pat. No. 7,226,434.

(60) Provisional application No. 60/840,363, filed on Aug. 25, 2006.

(51) Int. Cl.
*A61M 5/00* (2006.01)
*A61M 5/178* (2006.01)

(52) U.S. Cl.
USPC ...................................... 604/110; 604/164.01

(58) Field of Classification Search
USPC ............... 604/110, 162, 163, 164.01, 164.08, 604/187, 192, 195, 198, 263
See application file for complete search history.

(56) References Cited

U.S. PATENT DOCUMENTS 2,623,521 A  12/1952  Shaw
3,308,821 A   3/1967  Shields
(Continued)

FOREIGN PATENT DOCUMENTS

AU  2006200679 A1  2/2006
EP  0 750 915 A2  1/1997
(Continued)

OTHER PUBLICATIONS

The extended European Search Report corresponding to European Application No. EP 07 837 391.7, completed Jun. 27, 2012 and mailed Jul. 6, 2012; (6 Pages).

*Primary Examiner* — Laura Bouchelle
*Assistant Examiner* — Nathan R Price
(74) *Attorney, Agent, or Firm* — Lisa E. Winsor, Esq.

(57) ABSTRACT

A safety shield incorporating a locking clip to prevent inadvertent sticks or punctures by a needle is provided. The needle can be a needle cannula or other piercing member, disposed in a sliding orientation in the safety shield, such that the needle slides within the locking clip between an aperture at a proximal end of the locking clip and a trigger hole at a distal end of the clip. Upon withdrawal of the needle after use, a binding orientation is triggered when the needle tip is withdrawn from the trigger hole. As further protection to the bi-directional lock afforded by the binding orientation, the needle is provided with a safety stop to prevent movement of the needle tip through the aperture. In other aspects, the safety shield includes a trigger bushing, in which the needle cannula is slidably received, that is sized larger than the aperture.

13 Claims, 13 Drawing Sheets

(56) References Cited

U.S. PATENT DOCUMENTS

| | | |
|---|---|---|
| 3,610,240 A | 10/1971 | Harautuneian |
| 3,977,400 A | 8/1976 | Moorehead |
| 3,994,287 A | 11/1976 | Turp et al. |
| 4,000,739 A | 1/1977 | Stevens |
| 4,139,009 A | 2/1979 | Alvarez |
| 4,143,853 A | 3/1979 | Abramson |
| 4,160,450 A | 7/1979 | Doherty |
| 4,177,814 A | 12/1979 | Knepshield et al. |
| 4,211,214 A | 7/1980 | Chikashige |
| 4,261,357 A | 4/1981 | Kontos |
| 4,387,879 A | 6/1983 | Tauschinski |
| 4,424,833 A | 1/1984 | Spector et al. |
| 4,430,081 A | 2/1984 | Timmermans |
| 4,436,519 A | 3/1984 | O'Neill |
| 4,447,237 A | 5/1984 | Frisch et al. |
| 4,473,067 A | 9/1984 | Schiff |
| 4,475,548 A | 10/1984 | Muto |
| 4,512,766 A | 4/1985 | Vailancourt |
| 4,610,665 A | 9/1986 | Matsumoto et al. |
| 4,610,674 A | 9/1986 | Suzuki et al. |
| 4,626,245 A | 12/1986 | Weinstein |
| 4,629,450 A | 12/1986 | Suzuki et al. |
| 4,634,432 A | 1/1987 | Kocak |
| 4,649,904 A | 3/1987 | Krauter et al. |
| 4,655,752 A | 4/1987 | Honkanen et al. |
| 4,673,393 A | 6/1987 | Suzuki et al. |
| 4,705,511 A | 11/1987 | Kocak |
| 4,715,360 A | 12/1987 | Akui et al. |
| 4,722,725 A | 2/1988 | Sawyer et al. |
| 4,725,267 A | 2/1988 | Vaillancourt |
| 4,735,619 A | 4/1988 | Sperry et al. |
| 4,747,831 A | 5/1988 | Kulli |
| 4,758,225 A | 7/1988 | Cox et al. |
| 4,762,516 A | 8/1988 | Luther et al. |
| 4,781,692 A | 11/1988 | Jagger et al. |
| 4,781,693 A | 11/1988 | Martinez et al. |
| 4,795,432 A | 1/1989 | Karczmer |
| 4,798,594 A | 1/1989 | Hillstead |
| 4,809,679 A | 3/1989 | Shimonaka et al. |
| 4,817,631 A | 4/1989 | Schnepp-Pesch et al. |
| 4,846,809 A | 7/1989 | Sims |
| 4,857,062 A | 8/1989 | Russell |
| 4,874,377 A | 10/1989 | Newgard et al. |
| 4,895,346 A | 1/1990 | Steigerwald |
| 4,895,565 A | 1/1990 | Hillstead |
| 4,900,307 A | 2/1990 | Kulli |
| 4,904,242 A | 2/1990 | Kulli |
| 4,909,793 A | 3/1990 | Vining et al. |
| 4,909,798 A | 3/1990 | Fleischhacker et al. |
| 4,911,706 A | 3/1990 | Levitt |
| 4,917,668 A | 4/1990 | Haindl |
| 4,927,414 A | 5/1990 | Kulli |
| 4,929,234 A | 5/1990 | Chen |
| 4,931,044 A | 6/1990 | Beiter |
| 4,932,633 A | 6/1990 | Johnson et al. |
| 4,935,010 A | 6/1990 | Cox et al. |
| 4,944,725 A | 7/1990 | McDonald |
| 4,950,250 A | 8/1990 | Haber et al. |
| 4,950,257 A | 8/1990 | Hibbs et al. |
| 4,952,207 A | 8/1990 | Lemieux |
| 4,955,866 A | 9/1990 | Corey |
| 4,960,412 A | 10/1990 | Fink |
| 4,964,854 A | 10/1990 | Luther |
| 4,966,587 A | 10/1990 | Baumgart |
| 4,978,344 A | 12/1990 | Dombrowski et al. |
| 4,994,041 A | 2/1991 | Dombrowski et al. |
| 5,000,745 A | 3/1991 | Guest et al. |
| 5,013,304 A | 5/1991 | Russell et al. |
| 5,049,136 A | 9/1991 | Johnson |
| 5,051,109 A | 9/1991 | Simon |
| 5,053,017 A | 10/1991 | Chamuel |
| 5,085,645 A | 2/1992 | Purdy et al. |
| 5,085,648 A | 2/1992 | Purdy et al. |
| 5,108,374 A | 4/1992 | Lemieux |
| 5,126,090 A | 6/1992 | Egolf et al. |
| 5,135,504 A | 8/1992 | McLees |
| 5,147,327 A | 9/1992 | Johnson |
| 5,154,703 A | 10/1992 | Bonaldo |
| 5,171,229 A | 12/1992 | McNeil et al. |
| 5,183,468 A | 2/1993 | McLees |
| 5,195,983 A | 3/1993 | Boese |
| 5,215,528 A | 6/1993 | Purdy et al. |
| 5,322,517 A | 6/1994 | Sircom et al. |
| 5,322,518 A | 6/1994 | Schneider et al. |
| 5,328,482 A | 7/1994 | Sircom et al. |
| 5,334,158 A | 8/1994 | McLees |
| 5,338,311 A | 8/1994 | Mahurkar |
| 5,344,408 A | 9/1994 | Partika |
| 5,348,544 A | 9/1994 | Sweeney et al. |
| 5,364,387 A | 11/1994 | Sweeney |
| 5,370,623 A | 12/1994 | Kreamer |
| 5,390,898 A | 2/1995 | Smedley et al. |
| 5,409,461 A | 4/1995 | Steinman |
| 5,417,659 A | 5/1995 | Gaba |
| 5,419,766 A | 5/1995 | Chang et al. |
| 5,423,766 A | 6/1995 | Di Cesare |
| 5,425,884 A | 6/1995 | Botz |
| 5,466,223 A | 11/1995 | Bressler et al. |
| 5,514,100 A | 5/1996 | Mahurkar |
| 5,535,771 A | 7/1996 | Purdy et al. |
| 5,555,908 A | 9/1996 | Edwards et al. |
| 5,558,651 A | 9/1996 | Crawford et al. |
| 5,562,633 A | 10/1996 | Wozencroft |
| 5,572,516 A | 11/1996 | Miya et al. |
| 5,584,809 A | 12/1996 | Gaba |
| 5,584,810 A | 12/1996 | Brimhall |
| 5,584,818 A | 12/1996 | Morrison |
| 5,599,310 A | 2/1997 | Bogert |
| 5,601,536 A | 2/1997 | Crawford et al. |
| 5,672,161 A | 9/1997 | Allen et al. |
| 5,685,862 A | 11/1997 | Mahurkar |
| 5,690,619 A | 11/1997 | Erskine |
| 5,693,022 A | 12/1997 | Haynes |
| 5,700,249 A | 12/1997 | Jenkins |
| 5,702,369 A | 12/1997 | Mercereau |
| 5,718,688 A | 2/1998 | Wozencroft |
| 5,735,827 A | 4/1998 | Adwers et al. |
| 5,738,144 A | 4/1998 | Rogers |
| 5,788,215 A | 8/1998 | Ryan |
| 5,806,551 A | 9/1998 | Meloul et al. |
| 5,806,831 A | 9/1998 | Paradis |
| 5,814,098 A | 9/1998 | Hinnenkamp et al. |
| 5,817,069 A | 10/1998 | Arnett |
| 5,836,921 A | 11/1998 | Mahurkar |
| 5,853,393 A | 12/1998 | Bogert |
| 5,865,806 A | 2/1999 | Howell |
| 5,879,338 A | 3/1999 | Mahurkar |
| 5,891,105 A | 4/1999 | Mahurkar |
| 5,893,845 A | 4/1999 | Newby et al. |
| 5,911,705 A | 6/1999 | Howell |
| 5,928,162 A | 7/1999 | Giurtino et al. |
| 5,935,109 A | 8/1999 | Donnan |
| 5,947,930 A | 9/1999 | Schwemberger et al. |
| 5,954,313 A | 9/1999 | Ryan |
| 5,954,698 A | 9/1999 | Pike |
| 5,957,887 A | 9/1999 | Österlind et al. |
| 5,957,892 A | 9/1999 | Thorne |
| 5,967,490 A | 10/1999 | Pike |
| 5,967,698 A | 10/1999 | Pascoe |
| 5,980,488 A | 11/1999 | Thorne |
| 5,989,229 A | 11/1999 | Chiappetta |
| 6,001,080 A | 12/1999 | Kuracina et al. |
| 6,004,294 A | 12/1999 | Brimhall et al. |
| 6,068,011 A | 5/2000 | Paradis |
| 6,068,617 A | 5/2000 | Richmond |
| RE36,885 E | 9/2000 | Blecher et al. |
| 6,117,108 A | 9/2000 | Woehr et al. |
| 6,117,112 A | 9/2000 | Mahurkar |
| 6,132,401 A | 10/2000 | Van Der Meyden et al. |
| 6,171,284 B1 | 1/2001 | Kao et al. |
| 6,221,047 B1 | 4/2001 | Greene et al. |
| 6,224,569 B1 | 5/2001 | Brimhall |
| 6,280,399 B1 | 8/2001 | Rossin et al. |
| 6,280,401 B1 | 8/2001 | Mahurkar |

| Patent Number | Date | Inventor |
|---|---|---|
| 6,280,419 B1 | 8/2001 | Vojtasek |
| 6,287,278 B1 | 9/2001 | Woehr et al. |
| 6,322,537 B1 | 11/2001 | Chang |
| 6,361,525 B2 | 3/2002 | Capes et al. |
| 6,379,333 B1 | 4/2002 | Brimhall et al. |
| 6,406,459 B1 | 6/2002 | Allmon |
| 6,409,701 B1 | 6/2002 | Cohn et al. |
| 6,443,927 B1 | 9/2002 | Cook |
| 6,485,473 B1 | 11/2002 | Lynn |
| 6,500,129 B1 | 12/2002 | Mahurkar |
| 6,537,259 B1 | 3/2003 | Niermann |
| 6,551,287 B2 | 4/2003 | Hollister et al. |
| 6,582,402 B1 | 6/2003 | Erskine |
| 6,595,954 B1 | 7/2003 | Luther et al. |
| 6,595,955 B2 | 7/2003 | Ferguson et al. |
| 6,616,630 B1 | 9/2003 | Woehr et al. |
| 6,623,458 B2 | 9/2003 | Woehr et al. |
| 6,638,254 B2 | 10/2003 | Nakagami |
| 6,652,486 B2 | 11/2003 | Bialecki et al. |
| 6,652,490 B2 | 11/2003 | Howell |
| 6,663,592 B2 | 12/2003 | Rhad et al. |
| 6,673,047 B2 | 1/2004 | Crawford et al. |
| 6,682,510 B2 | 1/2004 | Niermann |
| 6,689,102 B2 | 2/2004 | Greene |
| 6,692,471 B2 | 2/2004 | Boudreaux |
| 6,699,221 B2 | 3/2004 | Vaillancourt |
| 6,740,063 B2 | 5/2004 | Lynn |
| 6,749,588 B1 | 6/2004 | Howell et al. |
| 6,761,704 B2 | 7/2004 | Crawford |
| 6,761,706 B2 | 7/2004 | Vaillancourt |
| 6,767,336 B1 | 7/2004 | Kaplan |
| 6,796,962 B2 | 9/2004 | Ferguson et al. |
| 6,802,490 B2 | 10/2004 | Leinsing et al. |
| 6,832,992 B2 | 12/2004 | Wilkinson |
| 6,855,128 B2 | 2/2005 | Swenson |
| 6,855,130 B2 | 2/2005 | Saulenas et al. |
| 6,902,546 B2 | 6/2005 | Ferguson |
| 6,916,311 B2 | 7/2005 | Vojtasek |
| 6,936,036 B2 | 8/2005 | Wilkinson et al. |
| 6,984,213 B2 | 1/2006 | Horner et al. |
| 7,004,927 B2 | 2/2006 | Ferguson et al. |
| 7,988,664 B2 * | 8/2011 | Fiser et al. .................... 604/110 |
| 2002/0151850 A1 | 10/2002 | Ferguson et al. |
| 2002/0193745 A1 | 12/2002 | Ferguson |
| 2003/0144627 A1 | 7/2003 | Woehr et al. |
| 2003/0195471 A1 | 10/2003 | Woehr et al. |
| 2003/0220617 A1 | 11/2003 | Dickerson |
| 2004/0078003 A1 | 4/2004 | Smith et al. |
| 2004/0092889 A1 | 5/2004 | Ferguson et al. |
| 2004/0133167 A1 | 7/2004 | Ferguson et al. |
| 2004/0236289 A1 | 11/2004 | Ferguson et al. |
| 2005/0027263 A1 | 2/2005 | Woehr et al. |
| 2005/0043691 A1 | 2/2005 | Ferguson |
| 2005/0059937 A1 | 3/2005 | Ferguson |
| 2005/0070855 A1 | 3/2005 | Ferguson et al. |
| 2005/0096592 A1 | 5/2005 | Carlyon et al. |

FOREIGN PATENT DOCUMENTS

| | | |
|---|---|---|
| EP | 0 750 915 A3 | 1/1997 |
| EP | 1 112 754 B1 | 2/2005 |
| JP | 2001514943 A | 9/2001 |
| JP | 2002248168 A | 9/2002 |
| JP | 2003506160 A | 2/2003 |
| WO | WO 96/22800 A1 | 8/1996 |
| WO | WO 97/42989 A1 | 11/1997 |
| WO | WO 02/076526 A2 | 10/2002 |
| WO | WO 2005/042073 A1 | 5/2005 |

* cited by examiner

LOCKING CLIP WITH TRIGGER BUSHING

This application is a continuation application of U.S. Application Ser. No. 11/895,597, filed Aug. 24, 2007, now U.S. Pat. No. 7,988,664, which is a continuation-in-part of U.S. application Ser. No. 10/585,987, filed on Oct. 31, 2006, now U.S. Pat. No. 7,736,332, which claims the benefit of, and priority to U.S. Provisional Application Ser. No. 60/840,363, filed on Aug. 25, 2006 and which is a national stage application of International Application No. PCT/US2004/036339, filed on Nov. 1, 2004, which is a continuation application of U.S. application Ser. No. 10/698,869, filed on Oct. 31, 2003, now U.S. Pat. No. 7,226,434. Each of these applications is incorporated herein in its entirety by reference for all purposes.

TECHNICAL FIELD

The present invention relates to safety devices for preventing inadvertent sticks and punctures by medical sharps, and more particularly, to a safety shield incorporating a locking clip with an integral binding plate that provides a hi-directional lock for a needle or other medical sharp.

BACKGROUND

Shielding devices of various types have been used to prevent inadvertent or undesired sticks from a contaminated piercing member such as a medical needle. Some devices utilize a separate shielding cap mounted over the needle after use, while other devices employ pivoting shields or extensible shields. Undesirably, these devices often require the practitioner to use both hands to manipulate or actuate the device. Other designs include retractable devices that have drawbacks such as excessive length, as compared to traditional non-safety devices, and which may require manual activation.

It would be desirable to provide a safety shield and locking clip capable of substantially preventing unlocking of the safety shield in a binding orientation, and thereby preventing unwanted needle exposure. It also would be desirable to provide a clip triggering mechanism interposed between the clip and the introducer needle/cannula. Such a triggering mechanism also is desirably configured to minimize sliding resistance between the introducer needle and the triggering mechanism when the locking clip is in the pre-actuated condition. The safety shield, locking clip and related methods should overcome the deficiencies of the presently available methods and systems.

SUMMARY

A locking clip, a safety shield incorporating the locking clip, and methods of making and using the safety shield and locking clip are disclosed. The safety shield is defined by a housing, and can be configured in a plurality of orientations, including at least a sliding orientation, in which a needle cannula is permitted to slide within the locking clip, and a binding orientation, in which the needle cannula is substantially restrained from proximal and distal movement in order to prevent re-exposure of the needle cannula after use, and thus prevent inadvertent sticks and punctures by the needle cannula. As used herein, "proximal movement" or "motion in a proximal direction" refers to motion or movement that is generally toward a clinician, and "distal movement" or "motion in a distal direction" refers to motion or movement that is generally away from the clinician or in the direction of the patient/subject.

As used herein, the terms "needle cannula" and "needle" are used interchangeably, and the needle cannula described with reference to the various embodiments can be replaced by a different type of needle, or another piercing member. Also, as used herein, the terms "locking clip" and "clip" are used interchangeably, and in particular, refer to a clip configured for use with the safety shield of the present invention.

Various clips can be used in conjunction with the safety shield, in accordance with the present invention. An exemplary clip can include a first leg, a second leg, and an aperture disposed between the first and second legs. The aperture can be formed on an aperture plate, also referred to herein as a "locking plate." The locking plate is particularly useful in the binding orientation for triggering a bi-directional lock, which can substantially restrain proximal or distal movement of the needle cannula. A distal end of the clip, i.e., that portion which is farthest from the clinician, can be formed with a trigger hole, dimensioned for movement of the needle cannula therethrough in the sliding orientation. The second leg of the clip can include[s] a bearing surface for engaging the needle cannula, and at least one spring element, or a network of spring elements, to facilitate convergent movement of the first and second legs.

The distal end of the clip also is formed with a clearance hole or opening. The clearance hole or opening is arranged with respect to the trigger hole, such that when the clip is put into the binding orientation, the needle cannula is disposed so as to be at least opposite to the clearance opening. In particular embodiments, a portion of the distal end of the needle cannula is disposed within the clearance opening or extends outwardly from the clearance opening. The clearance opening or hole also is dimensioned so that the needle cannula does not come into contact with edges of the clearance opening.

According to first and second examples or aspects of the clip of the present invention, the trigger hole is formed either as a separate hole from the clearance opening, or alternatively, as adjacent to or at least partially connected to the clearance opening, where the clearance opening can receive at least a portion of the needle cannula in the binding orientation. In the first exemplary embodiment or aspect, the trigger hole and the clearance opening constitute separate openings, thus forming a two-hole design such as that described in International Publication No. WO 2005/042073 referred to hereinafter, the teachings of which are incorporated herein by reference. In the second exemplary embodiment or aspect, the trigger hole and the clearance opening have at least some overlap, thus forming a single opening having a predetermined shape. As described further herein, such an opening is dimensioned and shaped so the needle cannula is slidable within the clip until the clip is put into the binding orientation. Other variations of the clip are possible, and the clip is not limited to the two-hole design or single opening described herein.

When the clip is in the binding orientation, the clip is secured to the needle cannula so as to form a bi-directional lock. In this way, there should be no relative movement between the clip and the needle cannula along the long axis of the needle cannula. In further embodiments, the clip and housing are respectively configured to cooperate so the clip remains engaged with or secured to the needle cannula even if the clinician or another attempts to move either the housing of the safety shield or the needle cannula in either a proximal or distal direction.

Notwithstanding this, it is contemplated that efforts might be taken to intentionally overcome the bi-directional locking by the clip so as to defeat the needle stick protection afforded by the safety shield. Thus, and in a first exemplary embodiment of the safety shield, the needle cannula is formed so as to include a safety stop (also referred to as a "safety stop feature," "stop member," and "safety stop member") located near or adjacent to a distal end of the needle cannula. The safety stop includes any of a number of mechanisms or techniques known to those skilled in the art, which would prevent passage of the distal end of the needle cannula through the aperture of the aperture/locking plate.

In further embodiments, the safety stop includes a localized depressed area in the needle cannula that extends generally outwardly from the exterior surface of the needle cannula (e.g., depression formed by crimping), an arcuate member secured about the exterior surface of the needle cannula (e.g., ferrule or ring), or other types of surface artifacts that in effect create a projection extending outwardly from at least one or more portions of the needle cannula exterior surface. Such surface artifacts, localized depressions, or arcuate members are sized and arranged on the needle exterior surface so that they create a radial projection from the exterior surface that is larger than the aperture hole in the aperture plate. In this way, even if one could create a condition that would momentarily allow the clip and needle to move with respect to each other, the needle cannula safety stop and aperture plate would cooperate to prevent the needle cannula from moving in a proximal direction or the safety shield housing moving in a distal direction to expose the sharp end of the needle cannula.

According to a further aspect or embodiment of the present invention, the safety shield includes a clip according to the second exemplary embodiment, a needle cannula having a stop member or feature and a trigger bushing. The stop member or feature can be formed in a manner similar to the safety stop described herein. In one embodiment the trigger bushing, which can have a generally tubular configuration, is inserted in the trigger hole of the clip. The needle cannula is arranged to pass through the trigger bushing and be slidable therein when the trigger bushing is disposed within the trigger hole. The stop member is generally sized and arranged on the needle cannula so as to create a radial projection from the exterior surface of the needle cannula that is larger than the lumen or inner diameter of the trigger bushing.

When it is desired to put the clip into the binding orientation, the needle cannula is moved proximally with respect to the safety shield (e.g., the clinician pulls back on the needle cannula). When the needle cannula is moved such that the stop member on the needle cannula contacts the trigger bushing, further relative proximal movement of the needle cannula also results in such movement by the trigger bushing. When the trigger bushing passes through the trigger hole, the needle cannula passes through the opening between the trigger hole and the clearance opening, thereby causing the clip to transition from the sliding orientation to the binding orientation. In this way, the clip is secured to the needle cannula to form the bi-directional lock such that there is no relative movement between the clip and the needle cannula.

As indicated herein, it is contemplated that efforts might be taken to intentionally overcome the bi-directional locking by the clip so as to defeat the needle stick protection afforded by the safety shield. As such, in further embodiments, the trigger bushing is sized or dimensioned so at least a portion of the trigger bushing is larger than the aperture hole in the aperture plate. Thus, even if one could create a condition that would momentarily allow the clip and needle to move with respect to each other, the trigger bushing and the aperture plate would cooperate to prevent the needle cannula from moving in a proximal direction or the safety shield housing moving in a distal direction to expose the sharp end of the needle cannula.

A method of using a safety shield according to the present invention includes steps of: providing a clip with at least a first leg having a trigger hole, a second leg, and an aperture disposed between the first and second legs; connecting at least a portion of the clip to a catheter hub; receiving a needle in a sliding orientation through the catheter hub; withdrawing the needle from the catheter hub and through the trigger hole, such that the portion of the clip becomes disconnected from the catheter hub, and triggering a lock that restrains movement of the needle; causing further movement of the needle with respect to the clip; and stopping a distal end of the needle from moving beyond the aperture. According to the method, the needle can be provided with a safety stop that prevents movement of the needle through the aperture. In addition, a trigger bushing can be provided to slidably enclose at least a portion of the needle and the trigger bushing being sized larger than the aperture.

Other aspects and embodiments of the invention are discussed below.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein.

DEFINITIONS

Figure 1:
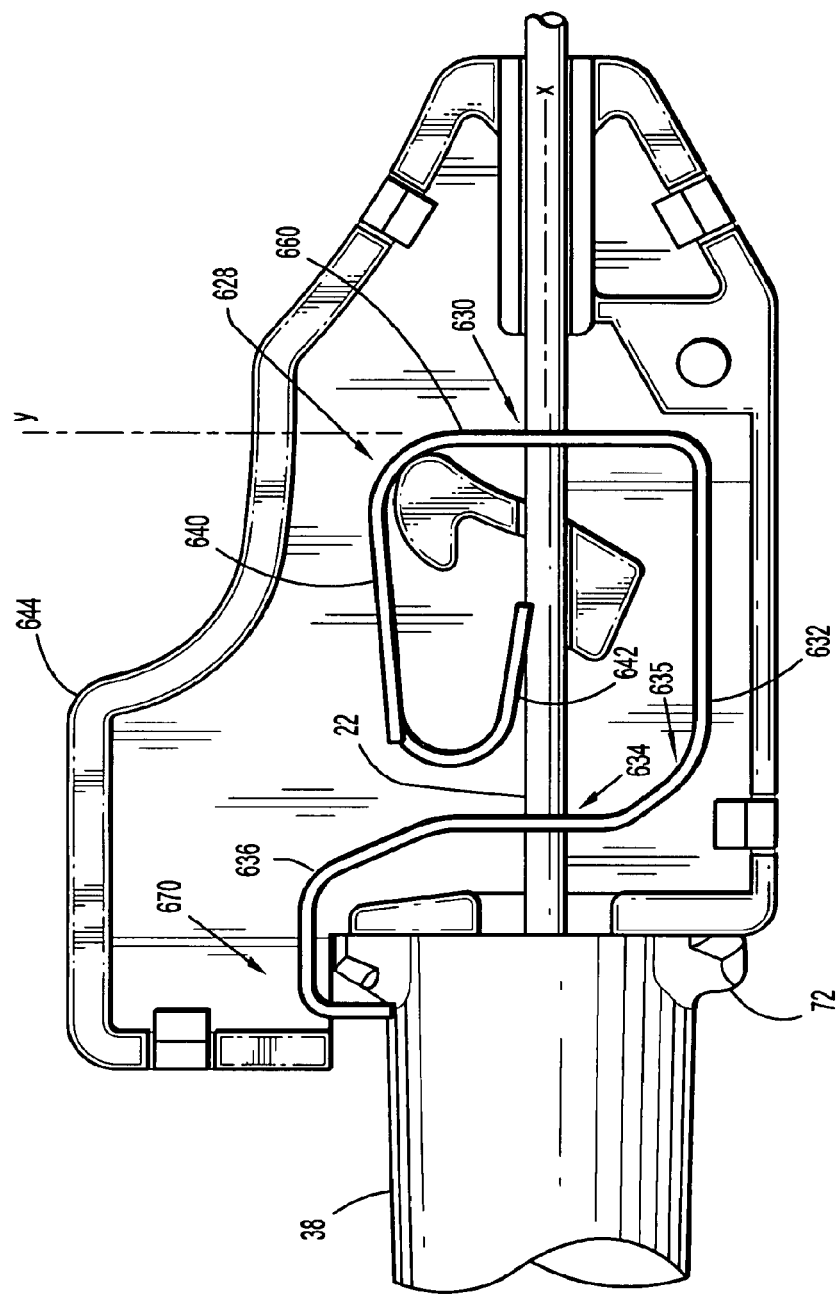
FIG. 1 is a cross-sectional side view of a safety shield including a locking clip according to a first exemplary embodiment of the present invention in the sliding orientation, where a catheter hub is coupled to the safety shield housing.

The instant invention is most clearly understood with reference to the following definitions:

As used in the specification and claims, the singular form "a", "an" and "the" include plural references unless the context clearly dictates otherwise.

As used herein, the term "subject" refers to a patient that receives infusions or has blood and/or fluid collected therefrom using a catheter, needle, or other device that includes a safety shield.

As used herein, the term "clinician" refers to an individual (e.g., doctor, nurse, technician or other medical personnel) administering an infusion, performing fluid sampling, installing or removing a needle cannula, and may include support personnel.

As used herein, the term "proximal" refers to a portion of a structure that is closer to a clinician, and the term "distal" refers to a portion that is farthest from the clinician.

DETAILED DESCRIPTION

A locking clip, a safety shield incorporating the locking clip, and methods of making and using the safety shield and locking clip are provided. The embodiments and examples of the locking clip, safety shield, and related methods as disclosed herein are discussed in terms of medical piercing members such as, for example, hypodermic needles, etc. for infusion of intravenous fluids, medical infusion or fluid sampling, and more particularly, in terms of a safety shield and locking clip used with a needle cannula that prevents hazardous exposure to a needle tip, including, for example, inadvertent needle sticks. It is envisioned, however, that the present disclosure finds application to a wide variety of cannula needles and devices for the infusion of preventive medications, medicaments, therapeutics, etc. to a subject. It is also envisioned that the present disclosure may be employed for collection of body fluids including those employed during procedures relating to phlebotomy, digestive, intestinal, urinary, veterinary, etc. It is contemplated that the safety shield may be utilized with other medical needle applications including, but not limited to, fluid collection, catheters, catheter introducers, guide wire introducers, spinal and epidural, biopsy, aphaeresis, dialysis, blood donor, Veress needles, Huber needles, etc.

A safety shield including a housing that supports a clip for restricting movement of a piercing member is described in PCT Application No. PCT/US2004/036339, published as International Publication No. WO 2005/042073. PCT Application No. PCT/US2004/036339, filed on Nov. 1, 2004 and its related U.S. patent application Ser. No. 10/698,869, filed on Oct. 31, 2003, are hereby incorporated by reference herein. Reference also should be made to International Publication No. WO 2005/042073 for further details of the design and function of the locking clip and safety shield not otherwise described herein.

An exemplary safety shield and clip are shown, for example, in FIGS. 19-26 of International Publication No. WO 2005/042073 ("the '073 publication"). The clip is formed with a trigger hole in a distal end thereof, and an integral binding plate is located at a proximal end relative to a clinician. The binding plate includes an aperture, which defines a sliding orientation (see FIG. 25 thereof), such that the aperture is configured for sliding movement of a needle cannula therethrough, or a binding orientation (see FIG. 26 thereof), which provides a bi-directional lock that locks the distal end of the needle cannula in a protected configuration. As described in the '073 publication, the binding orientation is actuated when the tip of the needle cannula passes through the trigger hole in the distal end of the clip and the locking clip is secured to the needle cannula such that there is no further relative movement between the needle cannula and the locking clip. Thus, as the locking clip is disposed within the housing of the safety shield, the clinician or another is thereby shielded from an inadvertent needle stick.

As also described in the '073 publication, the safety shield is designed so relative movement by one or both of the housing and the locking clip in either or both the proximal or distal directions after the bi-directional lock is established, does not cause the locking clip to become disengaged from the needle cannula (i.e., the needle cannula does not slide or move with respect to the locking clip). Such relative movement between the clip and housing could occur for example because the clinician may not realize that the locking clip has been put into the binding orientation and thus the clinician might continue to withdraw the needle cannula (i.e., pull on the needle hub in the proximal direction). As more particularly described in the '073 publication, the interior structure of the housing and the structure of the locking clip are respectively designed and arranged so the force securing the locking clip to the needle cannula is increased if such relative movement causes the locking clip to come into contact with portions of the housing interior structure.

Referring to FIGS. 1-3C of the present application, there is disclosed a safety shield assembly that includes a housing 644 and a clip 628 according to a first exemplary embodiment of the present invention. The safety shield assembly is a protective device that includes the housing 644 for receiving the locking clip 628, where the clip 628 is accommodated in a cavity of the housing. The components of the safety shield assembly can be fabricated from materials suitable for medical applications, for example, polymerics or metals, such as stainless steel, depending on the particular medical application and/or preference of a clinician. Semi-rigid and rigid polymerics are contemplated for fabrication, as well as resilient materials. However, one skilled in the art will realize that other materials and fabrication methods suitable for assembly and manufacture, in accordance with the present disclosure, also would be appropriate.

A needle cannula 22 or similar piercing member is received through a central bore in the housing 644 of the safety shield assembly. The needle cannula 22 has a hub (not shown), a distal end 26 and defines a longitudinal axis x. It is contemplated that the needle cannula 22 may be fabricated from stainless steel in a range of sizes, including but not limited to, about 14 to 26 gauge, although smaller or larger sizes can be used depending on the requirements of a particular application. The needle cannula 22 can be provided in various lengths, for example, about 2.6 to 4.1 inches, although smaller or larger sizes also are envisioned.

Figure 2A:
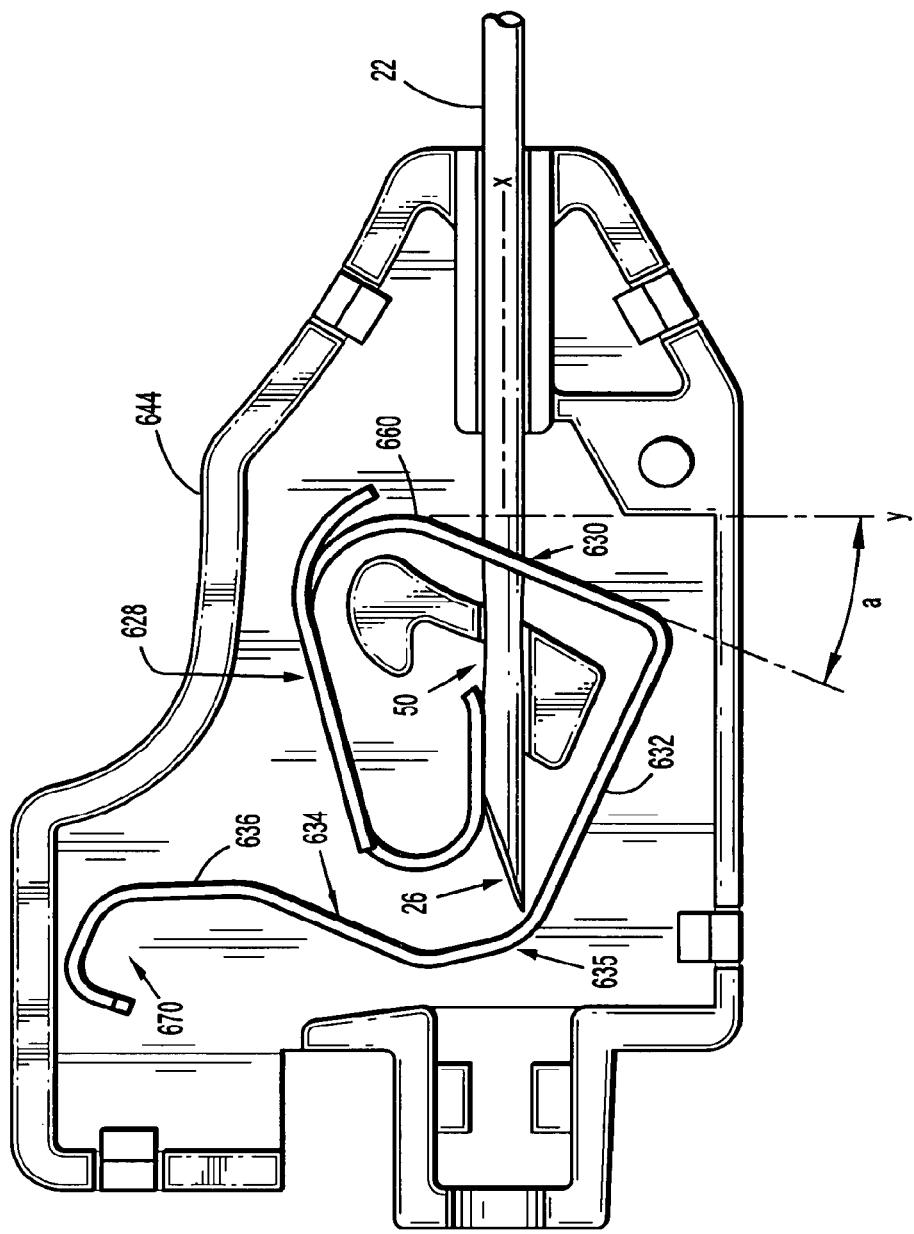
FIGS. 2A-2D are cross-sectional side views of the safety shield and locking clip of FIG. 1, where the catheter hub is released from the safety shield housing, and so the locking clip is in the binding orientation.
Figure 2A:
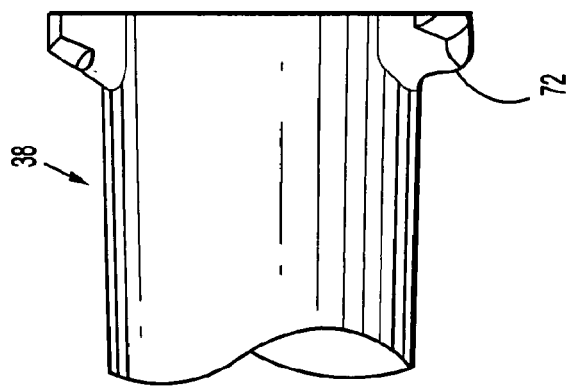
Figure 2B:
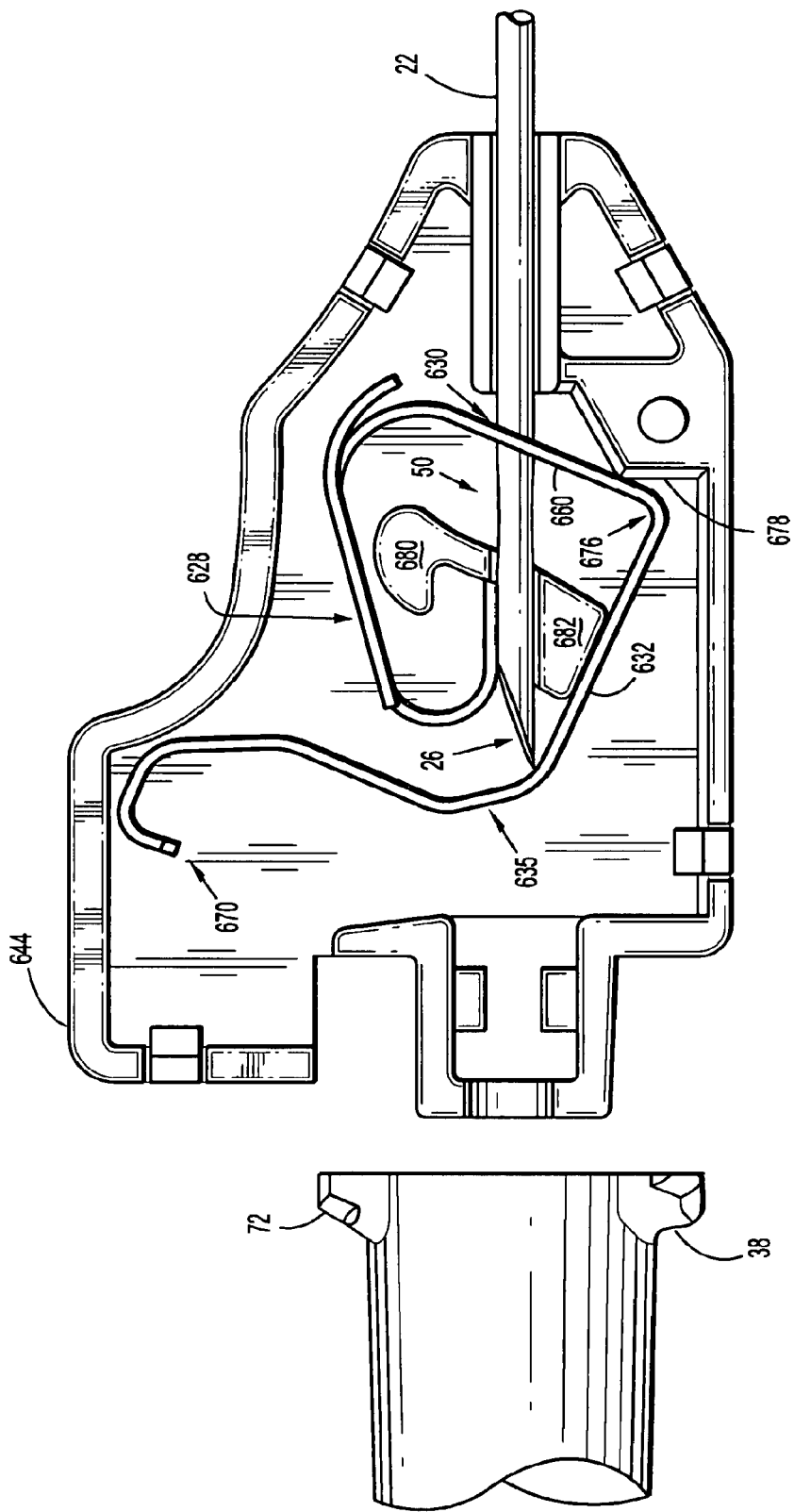
Figure 2C:
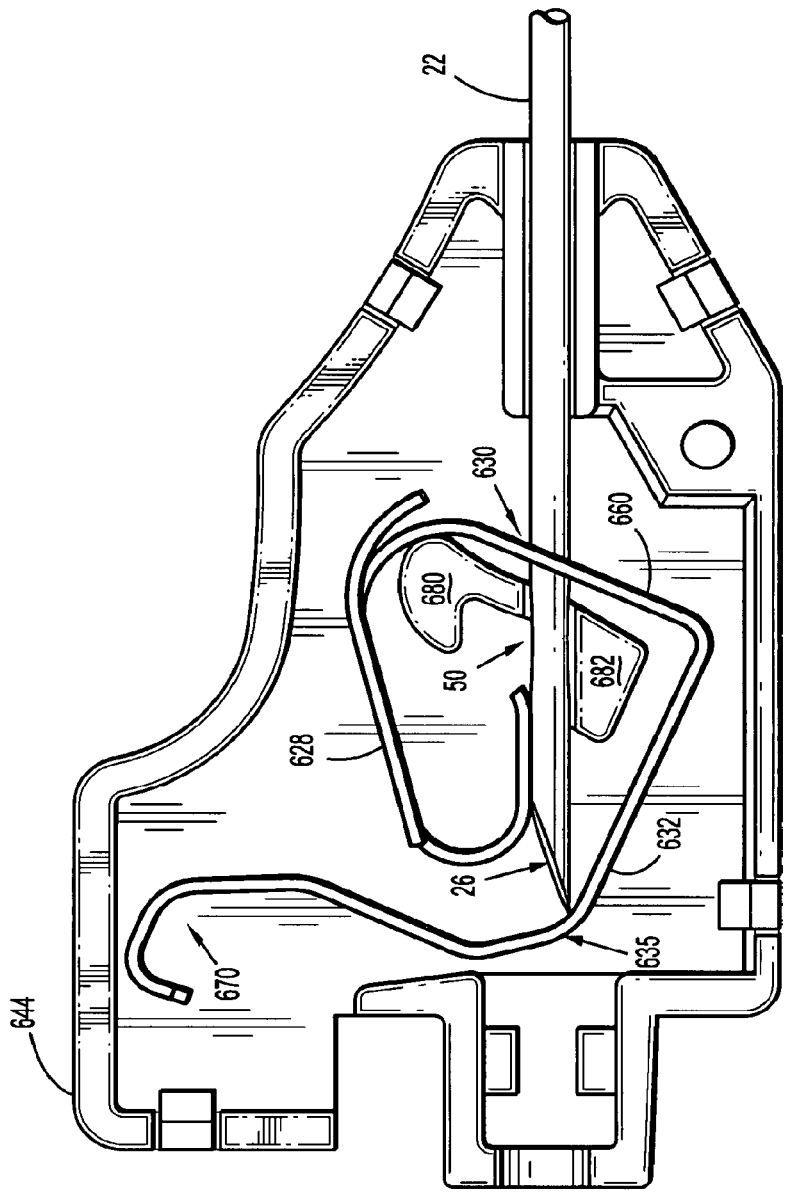
Figure 2C:
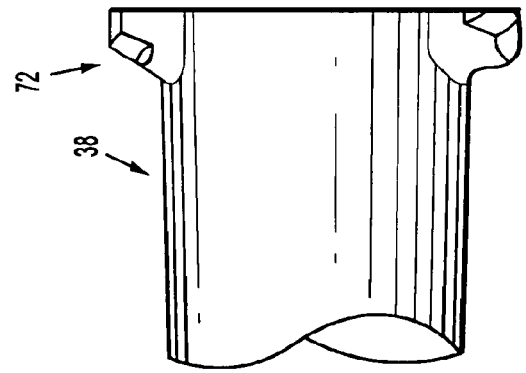
Figure 2D:
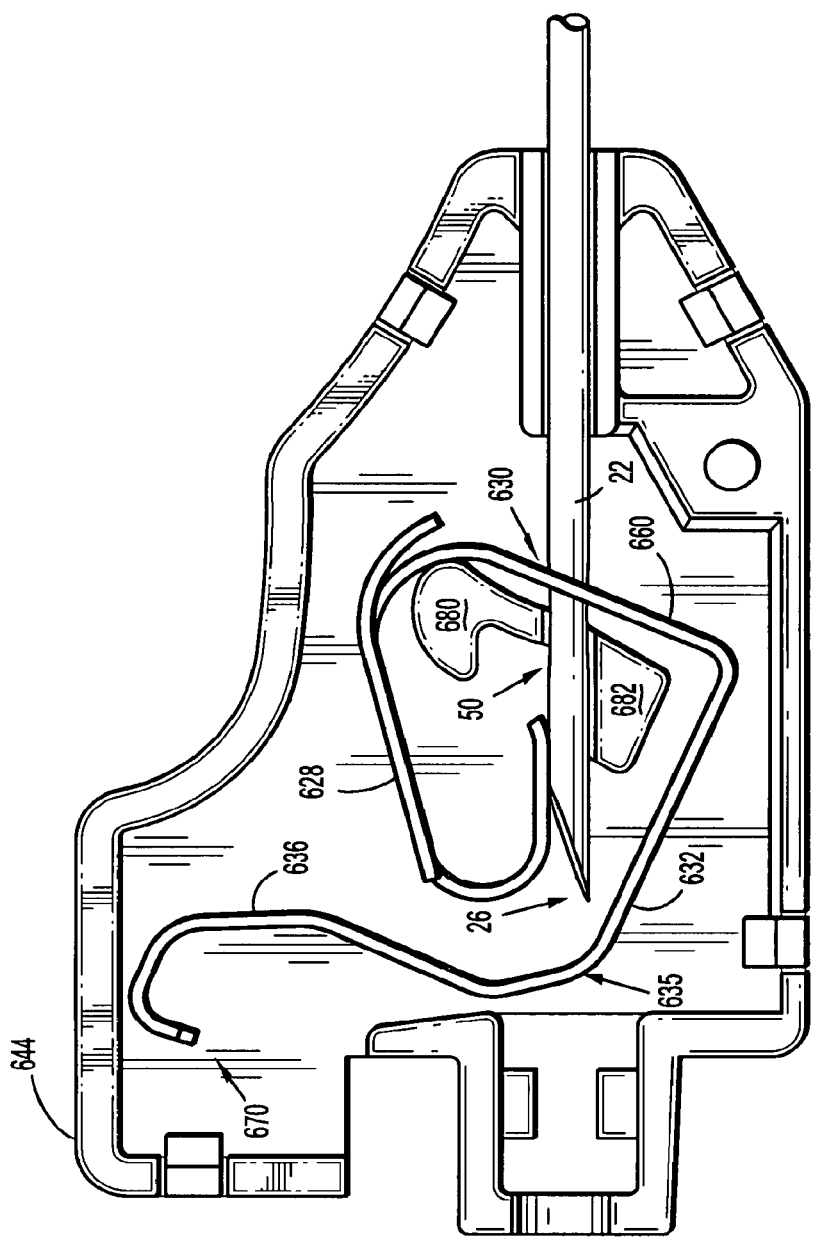
Figure 2D:
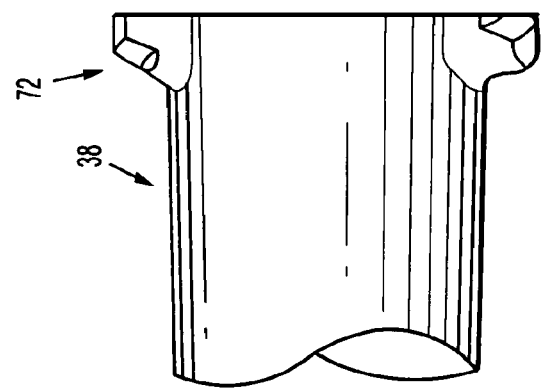
Figure 10:
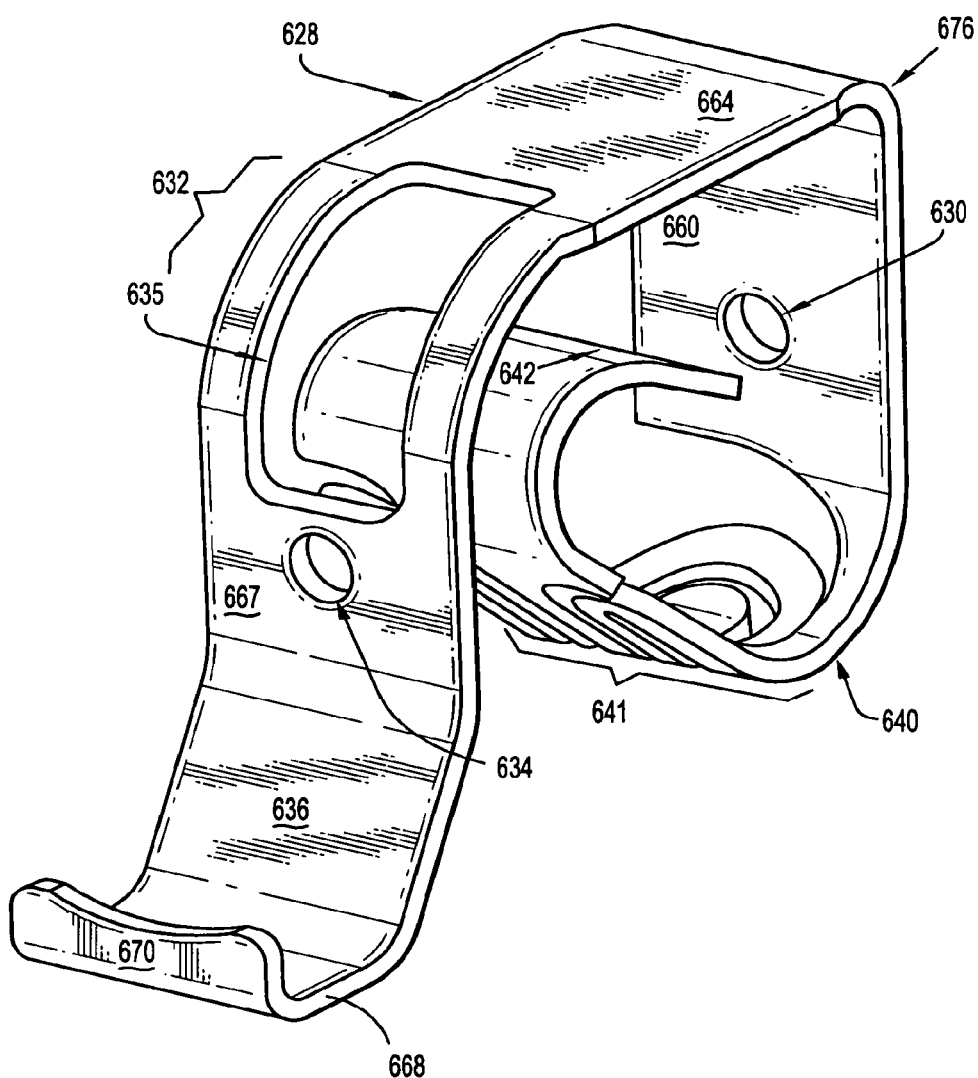
FIG. 10 is an enlarged perspective view of the first exemplary embodiment of a locking clip according to the present disclosure shown in FIG. 1.
Figure 11:
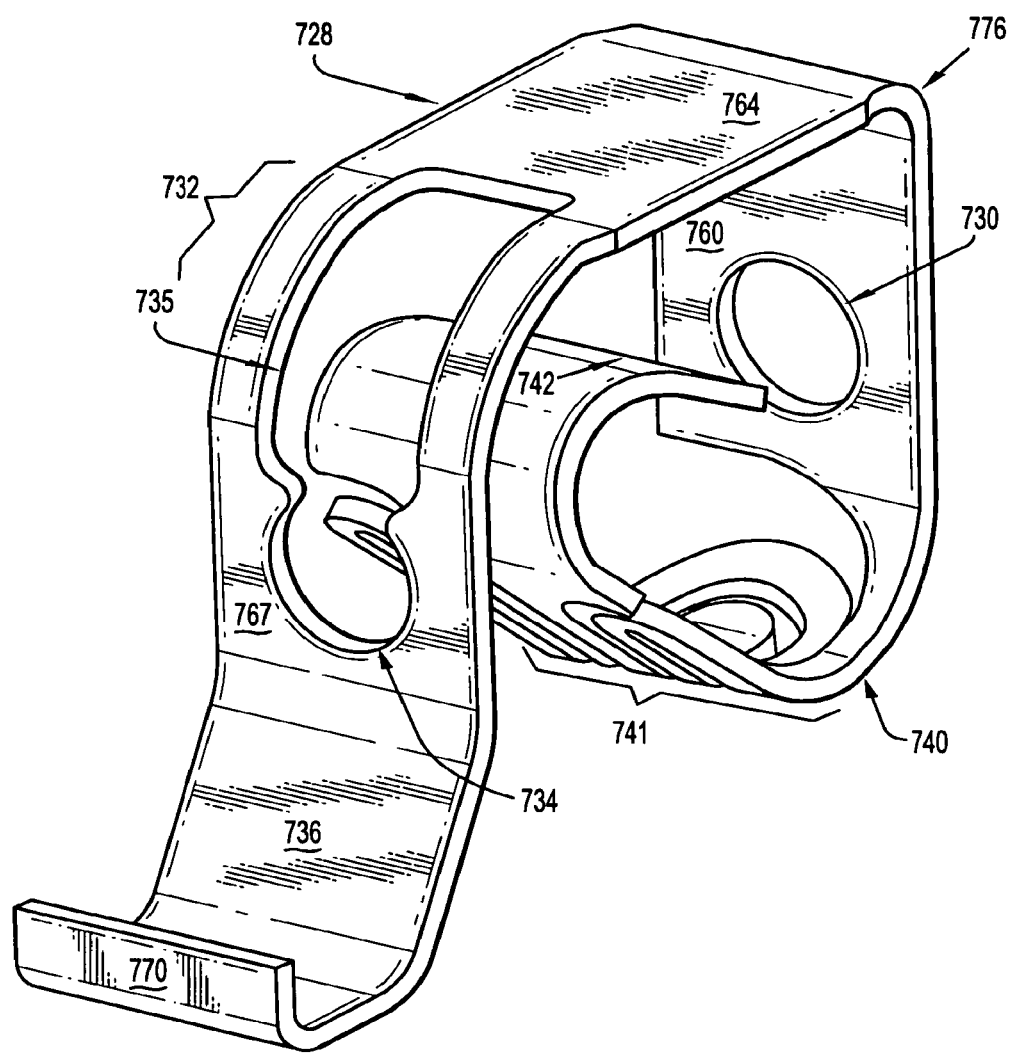
FIG. 11 is an enlarged perspective view of the second exemplary embodiment of a locking clip according to the present disclosure shown in FIG. 4A.

Examples of clips 628 and 728 suitable for use as a locking clip in the various embodiments of the present disclosure, for example, as the clip 628 depicted in FIGS. 1-2D, are shown in FIGS. 10 and 11. Like reference numbers are used to denote like components in the various figures as provided herein. In one embodiment, the clips 628 and 728 each are monolithically formed as a single integral piece of metal.

Referring to FIGS. 1-2D and 10, the clip 628 includes an aperture plate section 660 that defines the aperture 630. The aperture plate 660 has a rectangular, generally planar configuration with sufficient stiffness to produce forces for binding the clip to the needle cannula 22. The clip 628 also is disposed for rotational movement of the aperture plate 660 between a sliding orientation (FIG. 1), corresponding to axis y and a binding orientation (FIG. 2A), corresponding to an inclination a relative to axis y. The aperture 630 is dimensioned for slideable movement of the cannula therethrough and is oriented in an axis y which as shown is approximately perpendicular to the longitudinal axis x. In its sliding orientation, the aperture plate is oriented so that the edges of the aperture do not interfere with the sliding of the needle cannula 22 through the aperture. In other words, the aperture plate 660 is oriented so it crosses the longitudinal axis x at an angle that allows such slideable movement by the cannula.

In the binding orientation, the aperture plate 660 is rotated such that, when in the binding orientation, it is inclined to the inclination a with respect to the axis y, and thus also would be inclined with respect to the longitudinal axis x of the needle cannula. In the binding orientation, the edges of the aperture forcibly contact the outer surface of the needle cannula and prevent further sliding of the needle cannula through the aperture 630.

The clip 628 includes a first leg 632 that defines another aperture, such as for example, a trigger hole 634 dimensioned for movement of the needle cannula 22 therethrough (see FIG. 10). The first leg 632 has a distal part 636 that is configured to engage the catheter 38. The clip 628 includes a second leg 640 having a bearing surface 642 that engages needle cannula 22. The first leg 632 and second leg 640 are resiliently biased for convergent movement such that, when the distal end 26 or sharp tip of the needle cannula 22 is withdrawn from the trigger hole 634, the clip converges and the aperture plate 660 rotates until the aperture 630 is disposed in the binding orientation/position and the distal part 636 disengages the catheter 38 (see FIG. 2A). The first leg 632 also rotates in the plane of the clip, to the position shown in FIG. 2A.

The second leg 640 includes a network 641 (FIG. 10) that forms a continuous spring element to facilitate the resilient bias of the first and second legs 632, 640 and the resultant rotation of the aperture plate 660 and the first leg 632, and also exerts the force which causes the edges of the aperture 630 to contact the surface of the needle cannula and prevent further sliding of the needle cannula through the aperture 630. The network 641 is resiliently biased and includes biasing elements, such as, for example, spring elements that are connected to form a continuous network and may include channels therebetween (see FIG. 10). In effect, the network simulates an elongated spring lever arm while utilizing a much smaller space to contain the lever arm. This configuration advantageously provides more resilience without requiring additional material for fabrication, thereby improving manufacturing efficiency. The network 641 also reduces the stress concentrations on the clip 628, due to the continuous design, and reduces drag on the needle cannula 22 as it is withdrawn towards the trigger hole 634. The network 641 may include one or more spring elements.

The housing 644 contains the clip 628, and the housing 644 can include an outer surface, a top section, and a bottom section (see, e.g., FIGS. 1 to 2D). The housing 644 is movable between a retracted position and an extended position.

In the sliding orientation, as shown in FIG. 1, the first leg 632 extends distally from aperture plate 660. The first leg 632 has a proximal part 664 (FIG. 10) that is perpendicularly oriented relative to axis y of aperture plate 660 (see FIG. 10). The distal part 636 of the first leg 632 includes a transverse portion 667 that defines an aperture or trigger hole 634. The aperture or trigger hole 634 is formed within the transverse portion 667 for slideable engagement with the needle cannula 22 during movement between the retracted position and the extended position of the housing 644.

In the sliding orientation, the needle cannula 22 is disposed in the aperture or trigger hole 634 to prevent such convergent movement of the first leg 632. The distal part 636 defines an arm 668 that is configured to releasably retain the catheter hub with the outer surface of the housing 644. In the sliding orientation, the arm 668 is disposed such that a hook portion 670 thereof captures a flange 72 of the catheter hub (see FIG. 1).

As provided in International Publication No. WO 2005/042073, and in the present invention, first and second legs 632 and 640 are biased for convergent movement, which causes the first leg 632 to move transverse to the longitudinal axis x. While a portion of the first leg 632 does move traverse the axis of the needle cannula 22 in the course of its movement, the plane of movement of the first leg 632 is substantially parallel to the needle cannula 22, more particularly in a plane that is substantially parallel to and along the longitudinal axis x of the needle cannula. In other words, the needle cannula 22 actually lies in the plane of movement of the first leg 632. The same is true of the distal part 636 and the hook portion 670 of the first leg 632.

As shown in FIG. 2A, when the needle cannula 22 is withdrawn from the aperture forming the trigger hole 634, the distal part 636 rotates due to the bias of the first and second legs 632, 640 until the aperture plate 660 reaches the binding orientation. The hook portion 670 also rotates away from the catheter hub or needle cannula 22, as shown in FIG. 2A, to release the flange 72 of the catheter hub. The catheter 38 is then separable from the housing 644.

The distal part 636 also includes a clearance opening 635 disposed adjacent to the distal end 26 of the needle cannula 22. In the binding orientation, the distal end 26 is in alignment with the clearance opening 635 as illustrated in FIG. 2A. Also, and depending upon a number of factors such as the diameter of the needle cannula 22, the sharp tip at the distal end 26 of the needle cannula 22 may extend through the clearance opening 635. In addition, in the binding orientation the distal end 26 of the needle cannula 22 is spaced from the clearance opening 635 such that the distal end does not contact the inner surfaces of the clearance opening 635. In other words, the clearance opening 635 has a size that is greater than the diameter of the needle cannula 22.

Thus, the clearance opening 635 and the distal part 636 of the clip 628 do not block or impede the travel of the needle cannula 22 in a distal direction when in the binding configuration. As also indicated above, in at least some cases, the sharp tip 26 of the needle cannula 22 sticks out of the distal part 636 of the clip 628.

In the sliding orientation, the bearing surface 642 engages the outer surface of the needle cannula 22 to balance the convergent spring forces generated by the first and second legs 632, 640 and the network 641 of spring elements. Correspondingly, the first and second legs 632, 640 are balanced about the needle cannula 22 such that the aperture 630 of the aperture plate 660 is maintained in a sliding orientation. In the binding orientation, the needle cannula 22 passes out of the aperture or trigger hole 634 and the bearing surface 642 facilitates inclination of the clip 628. As the first and second legs 632, 640 converge due to the resilience of the spring elements of the network 641, the bearing surface 642 engages the needle cannula 22, causing the clip 628 to rotate relative to the longitudinal axis x (i.e., relative to the longitudinal axis of the needle cannula), putting the aperture 630 into the binding orientation with the needle cannula 22. The bearing surface 642 also engages the needle cannula 22 in the binding orientation to prevent movement of the needle cannula in the proximal and distal directions.

This binding configuration advantageously provides a bi-directional lock that locks the distal end 26 of the needle cannula 22 in a protected configuration. As can be seen from FIGS. 1-2A, the above configuration of the clip 628 also does not require operative engagement with the housing 644 to actuate the protective features of the clip.

The clip 628 also includes a transition portion 676 (FIG. 10) that connects the aperture plate 660 with the first leg 632. The transition portion 676 is configured to engage an inner surface 678 (FIG. 2B) of the housing 644 in the case where a clinician attempts to move the housing in a distal direction and/or withdraw the locked needle from the housing in a proximal direction, as illustrated in FIG. 2B. In particular embodiments, the inner surface 678 is disposed in parallel alignment with axis y. Such engagement of the transition portion 676 and the housing inner surface 678 augments the gripping engagement of the aperture 630 with the needle cannula 22 (e.g., the force locking the clip 628 to the needle cannula 22 is increased).

Similarly, the housing 644 includes internal structures 680, 682 that can be configured to engage correspondingly adjacent portions of the clip 628. For example, as shown in FIG. 2C, if the housing 644 happens to be pushed backwardly toward the hub of the needle (i.e., in the proximal direction), or if the needle 22 and clip 628 in the binding configuration are thrust forward in the housing 644 (i.e., in the distal direction), the clip 628 engages the internal structure of the housing 644 to prevent further forward movement of the clip 628 and the needle cannula 22, as well as re-exposure of the distal end 26.

The position of the clearance hole and/or the vertical dimension of the clearance hole 635 is adjusted so the distal end of the needle cannula or the needle is disposed in or opposite to the clearance opening when in the binding orientation. Since the size of the clearance opening is larger than the diameter of the needle, the first leg does not form a barrier to movement of the distal end of the needle in any direction. Thus, when the clip is in either the sliding configuration or the binding configuration, axial movement of the needle is neither blocked nor impeded by the trigger hole 634 or the clearance opening 635. Also, the distal end 26 of the needle remains spaced from the clearance opening 635 when the clip 628 is in the binding orientation even in the case where the user pushes backward on the housing 644, or forward on the needle hub.

As described above, when the clip 628 is in the binding orientation the clip forms a bi-directional lock that secures the clip to the needle cannula 22 so that there is essentially no relative movement between the clip and the needle cannula. The transition of the clip 628 from the sliding orientation to the binding orientation establishes the primary locking mechanism. Such a bi-directional lock formed by the clip in combination with the internal structure 678 (FIG. 2B), 680, 682 of the housing 644 provides a secondary guard against relative motion of the distal end 26 of the needle cannula 22 in either the proximal or distal directions. In this way, the sharp distal end 26 of the needle cannula 22 is prevented from exiting the housing 644, and thus from becoming re-exposed.

As also described above, the internal structure of the housing 644 also is arranged and configured so that contact between such housing structure 678, 680, 682 and the clip 628 does not cause the clip to become disengaged from the exterior surface of the needle cannula 22, thereby maintaining the bi-directional lock. In this way, relative movement between the needle cannula 22 and the housing 644 in either the distal or proximal directions does not cause the clip 628 to become disengaged from the needle cannula exterior surface. Thus, these structures 678, 680, 682 of the housing 644 and the clip 628 form a secondary mechanism or guard against the distal end 26 of the needle cannula 22 from becoming re-exposed.

In further embodiments of the safety shield assembly, see e.g., FIGS. 2D and 3A-3C, the needle cannula 22 is provided with a safety stop feature 50 (and alternatively 50b and 50c) that is near or adjacent to the distal end 26 of the needle cannula 22. The safety stop feature 50 is provided to deal with a highly unlikely situation where, due to intentional acts or unexpected contacts or impacts, a condition (i.e., a transient condition, force or load) is created after the binding orientation has been achieved between the clip and the needle cannula. Such a condition also would be of such a nature so as to cause the clip 628 and the needle cannula 22 to be capable of moving with respect to each other (i.e., so the needle cannula can move relative to the clip and the housing 644), thereby allowing further motion of the needle cannula in the proximal direction and/or motion of the housing in the distal direction.

In the case where such a condition was created, thereby allowing such relative proximal movement of the needle cannula 22 with respect to the housing to occur, then such relative proximal movement would be restrained in one of two ways: re-establishing the binding orientation between the clip and needle cannula, or when the safety stop feature contacts the clip aperture plate. If the safety stop feature has not contacted the aperture plate and the transient condition has dampened or abated sufficiently, then the clip and the needle cannula return to the binding orientation (i.e., bi-directional lock re-established), thereby preventing further relative movement between the clip and the needle cannula.

If the relative proximal movement of the needle cannula 22 causes the safety stop feature 50 to contact the aperture plate 630 such as shown in FIG. 2D, the increased diameter of the needle cannula in the horizontal direction prevents further movement of the needle cannula in the proximal direction. However, in that case the reduced diameter of the needle cannula in the vertical direction prevents the upper and lower edges of the aperture 630 from binding or grasping the needle cannula. Thus, while the stop feature 50 is in contact with the sides of the aperture 630, the needle cannula and the clip are not in a binding configuration.

If a force is applied to the clip or the needle which would impart distal movement of the needle relative to the clip, the stop feature does not prevent such movement. Rather, the needle moves to the point where the stop feature no longer contacts the sides of the aperture. At that point, however, the top and bottom edges of the aperture 630 will re-engage the top and bottom surfaces of the needle cannula, thus re-establishing a binding configuration and preventing further distal movement of the needle cannula relative to the clip. Thus, the safety stop feature 50 does not prevent or effect movement of the needle within the clip in the relative distal direction.

As shown in FIGS. 2A-2C, the safety stop feature 50 does nothing to block or not contact the aperture plate 630 or other clip or housing structure so as to restrain motion of the needle cannula 22 in the distal direction and/or motion of the housing 644 in the proximal direction (i.e., a bi-directional lock is not created between the safety stop feature and the aperture plate). Nor is there any other change in shape of the needle which prevents or effects such relative distal movement of the needle relative to the clip. Only the binding configuration of the top and bottom edges of the aperture 630 prevents such relative distal movement.

In general terms, the safety stop feature 50 is formed of one or more projections 52 (see FIG. 3A) that extend generally outwardly from the exterior surface of the needle cannula 22. These one or more projections are sized and arranged so that they create a radial projection from the needle cannula exterior surface such that the horizontal width of the needle cannula in this region becomes larger than the aperture 630 in the aperture plate 660. In particular, the safety stop feature 50 is a localized depressed or flattened area 54 (FIG. 3A) in the needle cannula 22, a portion of which extends generally outwardly from the exterior surface of the needle cannula. Such a portion thereby forms the one or more projections 52. Such a localized depressed or flattened area 54 can be formed, for example, by crimping the needle cannula 22.

When the clip 628 is activated so as to be in the binding condition or orientation, the needle cannula 22, including the safety stop feature 50, is withdrawn into the housing 644 and the safety stop feature is spaced from the aperture plate 660 (see FIG. 2A). It should be recognized that the safety stop feature 50 is not designed or intended to engage with or trigger the trigger hole 634 or any part of the clip so as to cause the clip to bind to the needle cannula (i.e., safety stop feature passes through the trigger hole without triggering the clip 628). As also shown in FIGS. 2B and 2C, the safety stop feature 50 also is spaced from the aperture plate 660 when there is relative movement between the housing 644 and the needle cannula 22 in either proximal or distal directions and when the clip 628 is in the binding orientation.

In sum, the bi-directional lock formed by the clip 628 itself forms the primary mechanism preventing the sharp tip or distal end 26 of the needle cannula 22 from being re-exposed, where the external structure of the housing 644 is the structure that prevents a clinician from contacting the sharp distal end 26 of the needle cannula 22. The housing internal structure and the clip structure are such as to prevent the clip 628 from becoming disengaged and thus form a secondary mechanism against the distal end 26 of the needle cannula 22 from becoming re-exposed. The needle cannula safety stop feature 50, in combination with the clip 628, forms a third mechanism whereby relative proximal motion of the needle cannula with respect to the housing 644 does not lead to re-exposure of the sharp distal end 26 of the needle cannula 22.

Figure 3A:
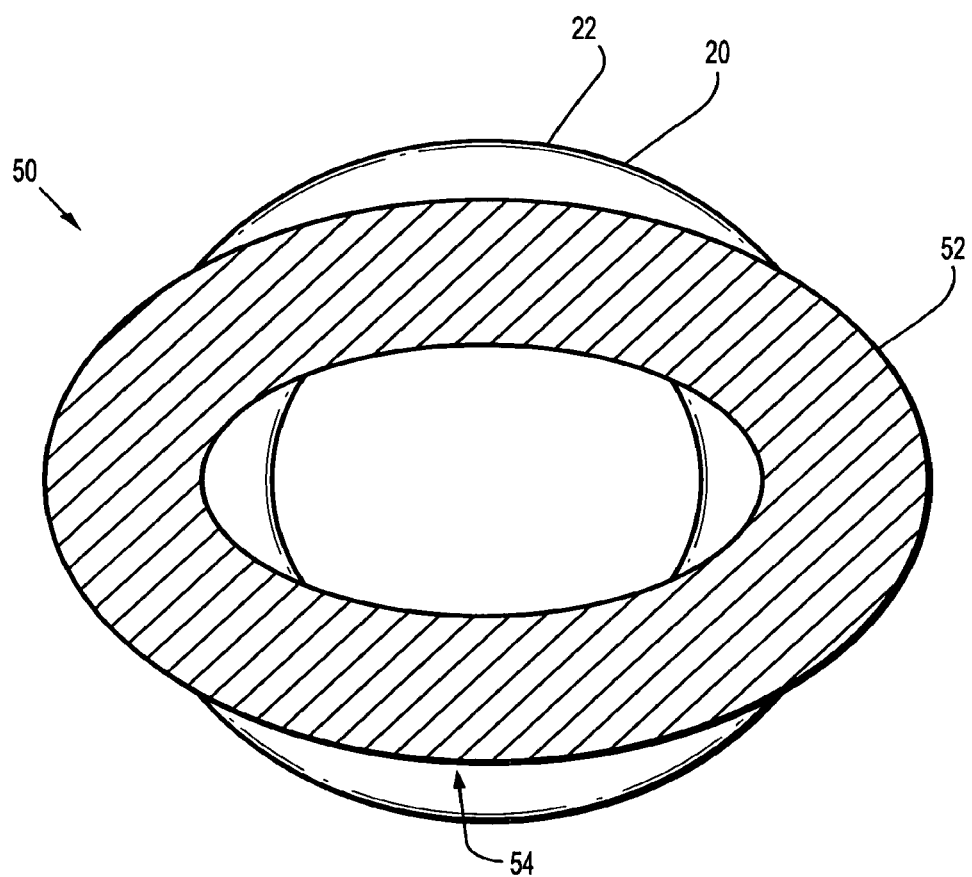
FIGS. 3A-3C are illustrations of various exemplary embodiments of a safety stop according to the present invention.
Figure 3B:
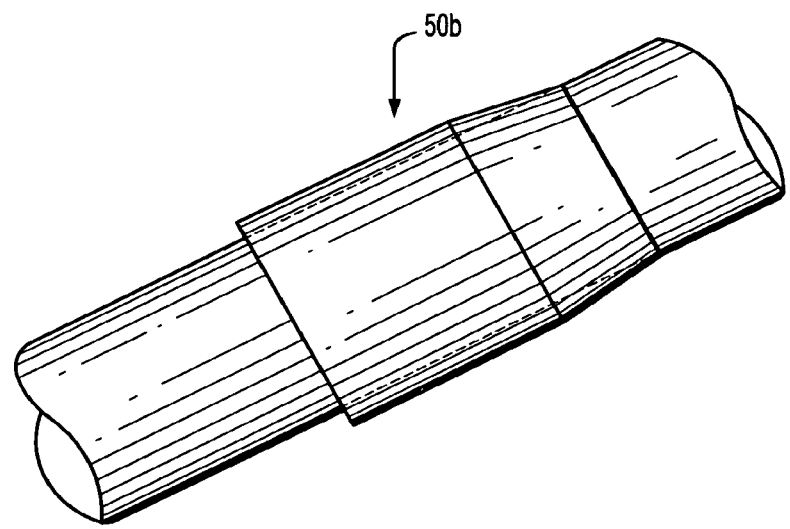

According to another exemplary embodiment, and with reference to FIG. 3B, an arcuate member(s) 50b (e.g., ferrule or ring) is secured about the exterior surface of the needle cannula, thereby forming the safety stop or feature. Although the arcuate member is depicted as being continuous about the circumference of the needle cannula, this is not a limitation as it is contemplated that one or more arcuate members are secured at different locations about the circumference and so each arcuate member extends along a portion of the circumference. Also, in further embodiments, and as shown in FIG. 3B, the leading edge of the arcuate member can be tapered or otherwise form a sloping surface; however, the leading edge can be essentially perpendicular to the exterior surface of the needle cannula. Each of the arcuate members shall have an arc length, height and axial length sufficient so that the member engages the aperture 630 and stops further movement of the needle cannula and/or locking clip with respect to each other.

Figure 3C:
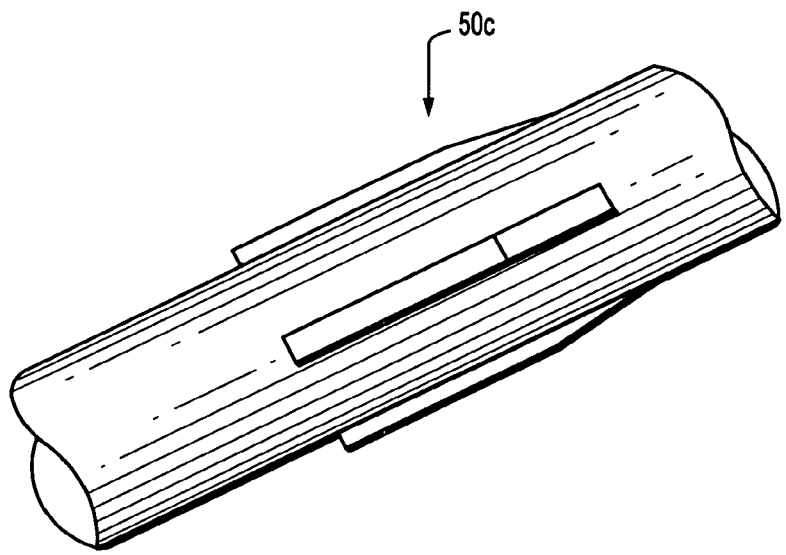

According to another exemplary embodiment, and with reference to FIG. 3C, one or more axially extending members 50c (e.g., rail like ferrule or ring) are secured to the exterior surface of the needle cannula thereby forming the safety stop or feature. In further particular embodiments, two or more axially extending members are provided and located so as to be equally spaced from each other about the circumference of the needle cannula. For example, a pair of axially extending members are provided and spaced from each other by about 180 degrees, three axially extending members are provided that are spaced from each other by about 120 degrees or four axially extending members are provided that are spaced from each other by about 90 degrees. Also, in further embodiments, and as shown in FIG. 3C, the leading edge of each axially extending member can be tapered or otherwise form a sloping surface; however, the leading edge can be essentially perpendicular to the exterior surface of the needle cannula. Each of the axially extending members shall have a width, height and axial length sufficient so that the member engages the aperture 630 and stops further movement of the needle cannula and/or locking clip with respect to each other.

In further exemplary embodiments, the safety stop includes a dimple having a diameter or at least a portion thereof larger than the aperture hole affixed or formed in the exterior surface of the needle cannula (e.g., a dimple formed by deposition of a soldering material or adhesive material) to prevent proximal movement of the distal end of the needle cannula 22 through the aperture hole 630. Further, the safety stop can be formed with at least two such dimples that are sized greater than the diameter of the needle cannula 22, where the dimple 50 should have a diameter larger than the aperture 630. The foregoing are exemplary and shall not be construed as limiting the safety stop to the specific examples illustrated and/or described herein.

A second example of a clip is shown in FIG. 11, where the clip 728 is similar in structure to the clip 628 depicted in FIG. 10. For example, the clip 728 includes first and second legs 732 and 740, and an aperture plate 760 defining an aperture 730. The first leg 732 includes a distal portion 736 that terminates in a hook portion 770 for capturing a flange 72 of the catheter hub. The first leg 732 includes a trigger hole 734 dimensioned for movement of the needle cannula therethrough in a sliding orientation. Extending in the proximal direction from the trigger hole 734 is a clearance opening 735 configured and arranged to receive the needle cannula in a binding orientation. The first and second legs 732 and 740 are resiliently biased for convergent movement by virtue of a network 741 of spring elements.

According to the clip 728 depicted in FIG. 11, the trigger hole 734 and the clearance opening 735 substantially overlap each other. In contrast, the clip 628 depicted in FIG. 10 has a separate trigger hole 734 and clearance opening 735, i.e., a two-hole design without any overlap. This arrangement is similar to that shown in International Publication No. WO 2005/042073.

FIGS. 4A to 9 depict a second exemplary embodiment or aspect of the present disclosure, in which a trigger bushing component is provided along with a needle cannula having a stop feature. The second exemplary embodiment of FIGS. 4A to 9 functions in a manner similar to the first exemplary embodiment of FIGS. 1-3C, but where the trigger bushing component and the stop feature cooperate as herein described to cause the triggering of the locking clip so the locking clip transitions form the sliding orientation to the binding orientation. Also, and as described herein, in the second exemplary embodiment, the trigger bushing component is sized so that it contacts the housing 644 of the safety shield or contacts the aperture/locking plate, thereby preventing withdrawal of the distal end of the needle cannula through the aperture in the aperture/locking plate when the locking clip is in the binding orientation.

Figure 4A:
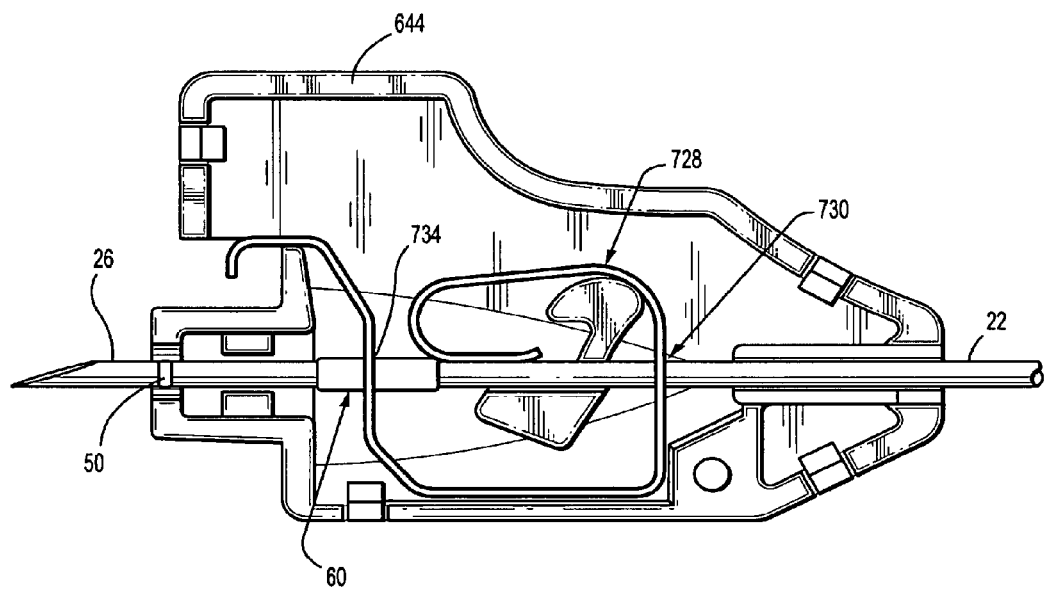
FIG. 4A is a cross-sectional side view of a safety shield and locking clip in a sliding orientation according to a second exemplary embodiment of the present invention.
Figure 4B:
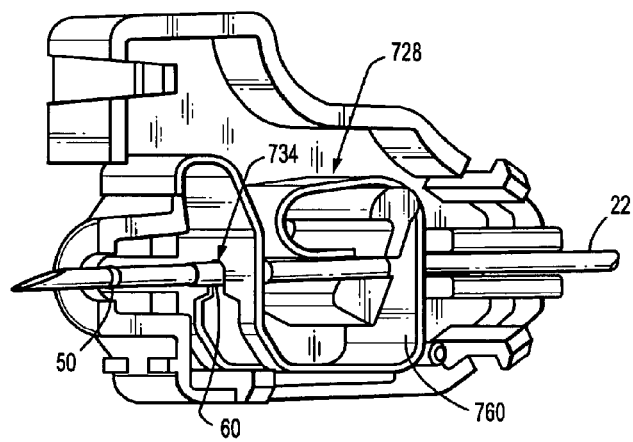
FIG. 4B is a perspective view of the safety shield and locking clip of FIG. 4A.

Referring to FIGS. 4A-4B, a trigger bushing 60 is generally tubular in configuration, and is placed in the trigger hole 734 of the clip 728 when the clip is in the sliding orientation. For illustration purposes, in FIGS. 4A to 9, the clip 728 depicted in FIG. 11 has been selected as the locking clip, although the clip 628 of FIG. 10 could be substituted therefor, in accordance with the present disclosure. In embodiments utilizing a needle having a stop member and a trigger bushing, the trigger bushing 60 can be placed in the trigger hole 734, and then the needle cannula 22 is inserted through the aperture 730 of the aperture/locking plate 760 and through a lumen of the trigger bushing.

As shown in FIGS. 4A-4B, the clip 728 and safety shield are provided in the sliding orientation, such that the needle cannula 14 can slide easily through the housing 644 of the safety shield. The trigger bushing 60 is provided to fit within the trigger hole 734 in the sliding orientation, and has an inner diameter greater than the outer diameter of the needle cannula 22, allowing the needle cannula 22 to slide in the lumen therethrough in the sliding orientation. In particular embodiments, the trigger bushing 60 is retained within the trigger hole so that it does not generally move axially when the locking clip is in the sliding orientation.

Similar to the first exemplary embodiment of FIGS. 1-3C, the stop member 50 provided on the needle cannula 22 in the second exemplary embodiment should be sized so as to prevent passage of the distal end 26 of the needle cannula 22 through the lumen in the trigger bushing 60. The stop member 50 also should have a diameter or portion thereof larger than the lumen and smaller than the trigger hole 734. In the second exemplary embodiment, the stop member does not contact the aperture/locking plate.

In the sliding orientation of FIGS. 4A-4B, when the needle cannula 22 is pulled back and withdrawn through the trigger hole 734, it slides within the trigger bushing until the stop member 50 contacts the trigger bushing 60. Thereafter, further movement of the needle cannula 14 in the proximal direction also causes the trigger bushing 60 to slide within the trigger hole 734 in the proximal direction. When a distal end of the trigger bushing 60 is pulled back through the trigger hole 734, the locking clip 728 moves into the binding orientation, as depicted in FIGS. 5A-5B.

Figure 5A:
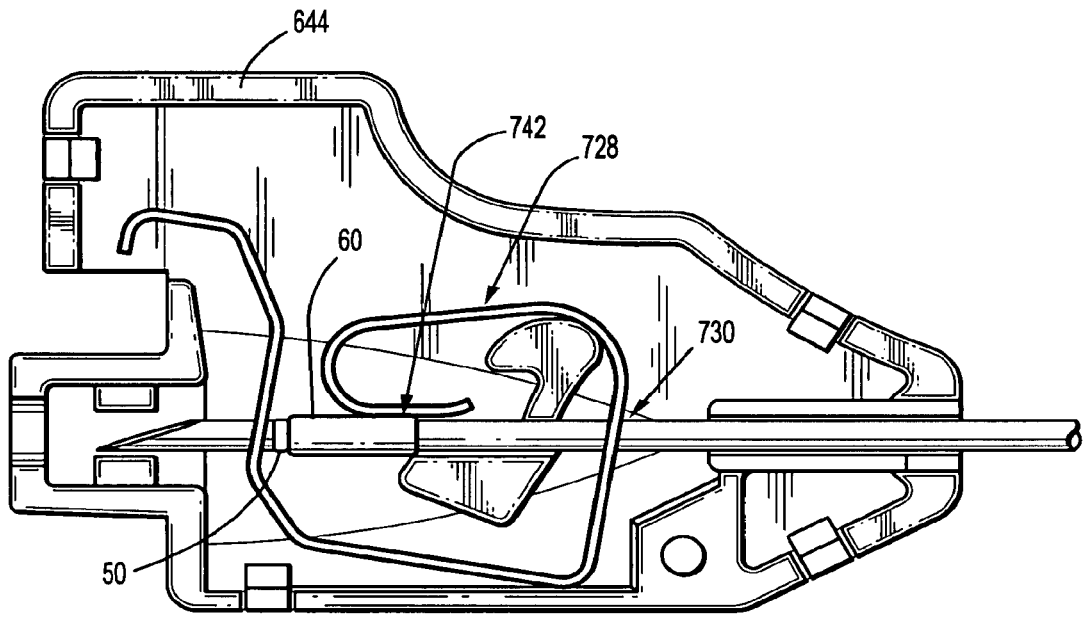
FIG. 5A is a cross-sectional side view of the safety shield and locking clip of FIG. 4A in a binding orientation.
Figure 5B:
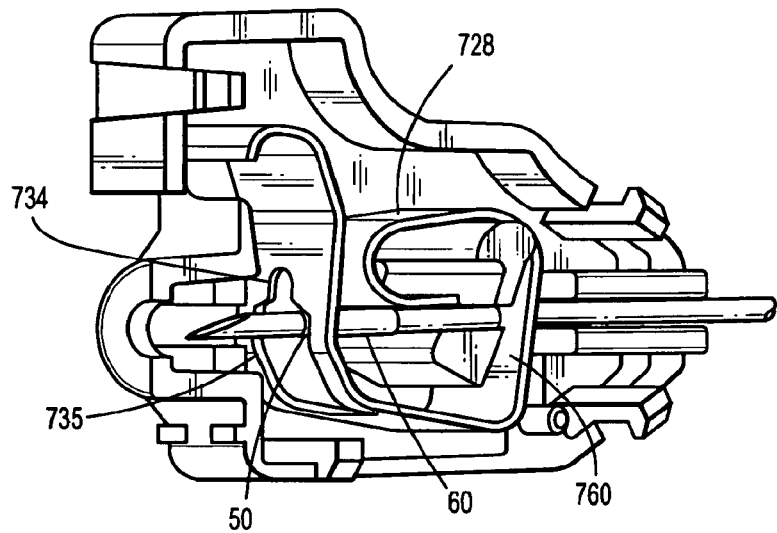
FIG. 5B is a perspective view of the safety shield and locking clip of FIG. 5A.

In the binding orientation of FIGS. 5A-5B, the distal end 26 of the needle cannula 22 is disposed in the clearance opening 735. In this state, a bi-directional lock is engaged, thereby restraining movement of the needle cannula 22. As shown in FIGS. 5A-5B, the aperture plate 760 is inclined relative to the sliding orientation of FIGS. 4A-4B, and the bearing surface 742 facilitates inclination of the clip 728. Resistance to re-exposure of the needle cannula 22 is provided due to the presence of the aperture/locking plate 760, in which the aperture engages with the exterior surface of the needle cannula thereby forming the bi-directional lock.

Proximal motion of the needle cannula 22 is resisted through at least three mechanisms. The bi-directional lock provides the primary guard against motion of the distal end 26 of the needle cannula 22 in either the proximal or distal directions. The secondary guard against such motion in either the proximal or distal direction is the structure of the interior of the housing and the structure of the locking clip. Such structures cooperate so distal or proximal motion of the needle cannula does not cause the locking clip to disengage from the needle cannula exterior surface. As indicated herein, the present disclosure includes a safety stop mechanism that prevents the needle tip from becoming exposed in the case where one conceived of a means that would allow the locking clip and needle cannula to move with respect to each other thereby allowing further motion of the needle cannula in the proximal direction and/or motion of the housing in the distal direction. As described below, at least one of the following two mechanisms can be provided in conjunction with the safety shield to stop such further unwanted movement of the distal end of the needle cannula in the proximal direction.

Figure 6:
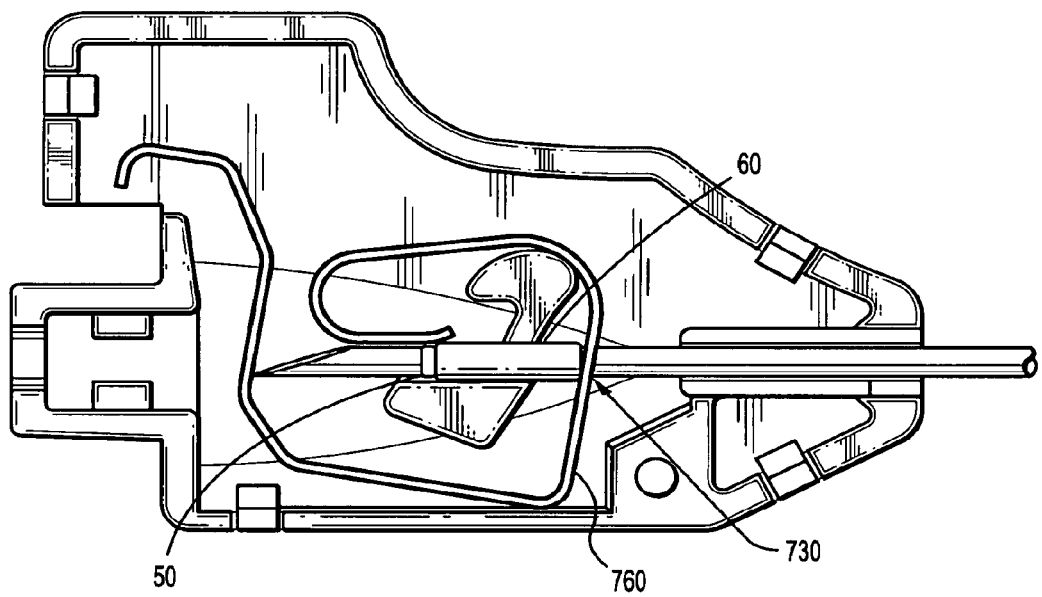
FIG. 6 is a cross-sectional side view of the safety shield and locking clip of FIG. 4A in a binding orientation, in which the needle cannula is further withdrawn in the proximal direction, so the trigger bushing contacts the locking plate.
Figure 7:
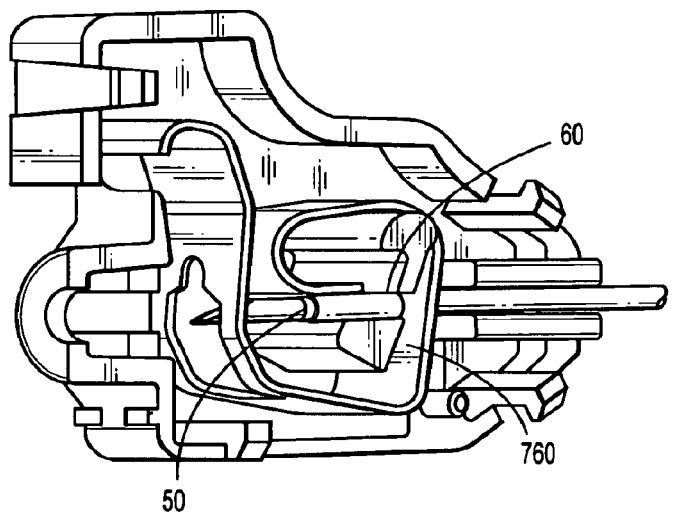
FIG. 7 is a perspective view of the safety shield and locking clip of FIG. 7.

FIGS. 6 and 7 depict different views of a first mechanism for preventing further proximal movement of the distal end 26 of the needle cannula 22. As shown in FIG. 6, the trigger bushing 60 moves back until it contacts the aperture/locking plate 760. In this case, the diameter of the trigger bushing 60 is greater than the aperture 730 and thus, the distal end 26 of the needle cannula 22 is prevented from moving through the aperture 730. Therefore, the presence of the stop member 50 and the trigger bushing 60 abutting against the aperture/locking plate 760 provides a physical barrier to block further proximal movement of the distal end 26 of the needle cannula 22. As a result, the distal end of the needle and the needle tip are prevented from moving proximally beyond the aperture and thus out of the housing.

Figure 8:
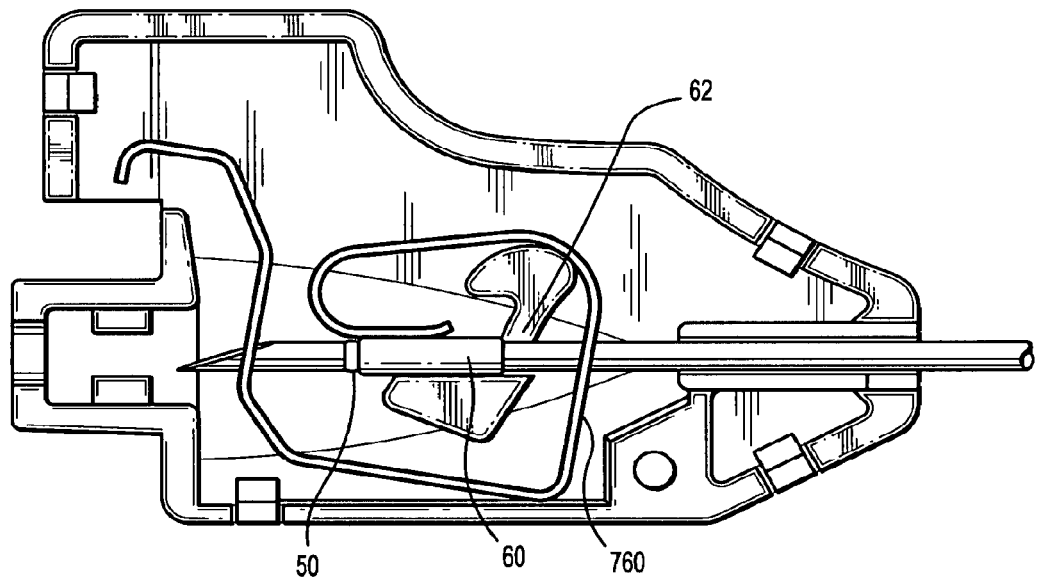
FIG. 8 is a cross-sectional side view of the safety shield and locking clip of FIG. 4A in a binding orientation, in which the needle cannula is further withdrawn in the proximal direction, so the trigger bushing contacts a portion of the shield housing.
Figure 9:
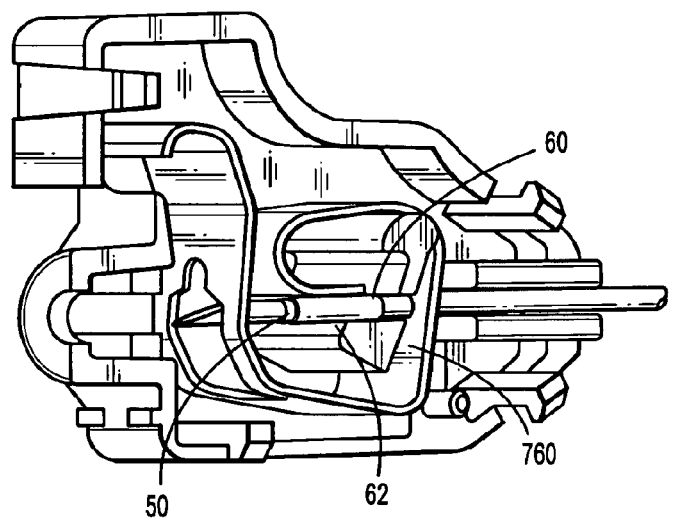
FIG. 9 is a perspective view of the safety shield and locking clip of FIG. 6.

FIGS. 8 and 9 depict different views of a second mechanism for preventing further proximal movement of the distal end 26 of the needle cannula 22. As shown in FIG. 8, the trigger bushing 60 moves back until it contacts a portion 62 of the housing 664 making up the safety shield. Because the trigger bushing 60 is against at least the portion 62 of the housing, the distal end 26 of the needle cannula 22 is stopped from further proximal movement. Therefore, the presence of the stop member 50 and the trigger bushing 60 abutting against or contacting the portion 62 of the housing provides a physical barrier to block further proximal movement of the distal end 26 of the needle cannula 22. Accordingly, the distal end and the needle tip cannot move proximally out of the housing.

In view of the foregoing, in a further embodiment, when the needle cannula includes a safety stop member such as that shown in FIG. 1, the safety shield housing is configurable so that the safety stop member contacts at least a portion of the housing thereby essentially preventing the distal end 18 of the needle cannula from moving further proximally. Accordingly, the distal end and the needle tip cannot move proximally beyond or out of the housing.

As described in the above exemplary embodiments of the safety shield, the needle cannula or other piercing member can be provided with at least a safety stop member, or at least a stop member and trigger bushing such that in a binding orientation, further movement of a distal end of the needle cannula in the proximal direction is essentially prevented. According to the present disclosure, the safety stop member and/or the trigger bushing abut against either the aperture/locking plate or a portion of the safety shield housing. In this way the aperture/locking plate or the housing provide a physical barrier to block further proximal motion of the needle and thus the needle point. The present disclosure also encompasses methods of forming the safety stop member/feature or the stop member/feature on the needle cannula, and inserting the trigger bushing in the trigger hole, and methods of using a safety shield provided in accordance with the above-described features.

Although embodiments of the disclosure have been described using specific terms, such description is for illustrative purposes only, and it is to be understood that changes and variations may be made without departing from the spirit or scope of the following claims.

INCORPORATION BY REFERENCE

The entire contents of all patents, published patent applications and other references cited herein are hereby expressly incorporated herein by reference in their entireties.

What is claimed is:

1. A safety shield incorporating a clip, comprising:
a housing defining a cavity dimensioned to receive the clip;
the clip including a body having a first leg, a second leg, an aperture disposed between the first and second legs, and a trigger hole formed within the first leg, the clip being movable from a sliding orientation to a binding orientation;
a needle received in the housing and being slidable through the trigger hole and the aperture of the clip when the clip is disposed in the sliding orientation;
a bushing movably positioned about the needle and positioned in the trigger hole when the clip is disposed in the sliding orientation; and
a stop member supported on the needle to move the bushing from within the trigger hole upon engagement with the bushing to allow the clip to move to the binding orientation.

2. The safety shield of claim 1, wherein the clip body includes a plate, the aperture being formed in the plate, wherein the plate is configured to engage and lock the needle in the binding orientation.

3. The safety shield of claim 1, wherein the stop member includes at least one projection positioned on an exterior surface of the needle.

4. The safety shield of claim 3, wherein the at least one projection is positioned adjacent a distal end of the needle.

5. The safety shield of claim 1, wherein in the binding orientation, the bushing abuts against a plate defining the aperture to prevent withdrawal of a distal end of the needle through the aperture.

6. The safety shield of claim 1, wherein in the binding orientation, the bushing abuts against a portion of the housing to prevent withdrawal of a distal end of the needle through the aperture.

7. The safety shield of claim 1, further including a clearance opening adjacent to the trigger hole, a distal end of the needle being received in the clearance opening in the binding orientation.

8. The safety shield of claim 7, wherein the clearance opening and the trigger hole form a single opening.

9. The safety shield of claim 1, wherein the first leg of the clip terminates in a hook portion for engaging a catheter hub external to the safety shield.

10. The safety shield of claim 9, wherein the hook portion of the clip releasably engages the catheter hub in the sliding orientation.

11. The safety shield of claim 1, wherein the second leg of the clip includes a spring member for biasing the first and second legs for convergent movement.

12. The safety shield of claim 11, wherein the second leg of the clip includes a bearing surface for contacting the needle.

13. The safety shield of claim 1, wherein the needle is a needle cannula.

* * * * *